(12) United States Patent
Saur et al.

(10) Patent No.: US 12,322,096 B2
(45) Date of Patent: Jun. 3, 2025

(54) MULTI-TASK LEARNING OF WHITE LIGHT PHOTOGRAPHS FOR A SURGICAL MICROSCOPE

(71) Applicant: Carl Zeiss Meditec AG, Jena (DE)

(72) Inventors: Stefan Saur, Aalen (DE); Marco Wilzbach, Aalen (DE); Alexander Freytag, Erfurt (DE); Anna Alperovich, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 401 days.

(21) Appl. No.: 17/807,056

(22) Filed: Jun. 15, 2022

(65) Prior Publication Data

US 2022/0405926 A1 Dec. 22, 2022

(30) Foreign Application Priority Data

Jun. 16, 2021 (DE) .......................... 10202111588.6

(51) Int. Cl.
*G06T 7/00* (2017.01)
*A61B 5/00* (2006.01)
*G16H 50/20* (2018.01)

(52) U.S. Cl.
CPC .......... *G06T 7/0012* (2013.01); *A61B 5/0071* (2013.01); *G16H 50/20* (2018.01); *G06T 2207/30024* (2013.01)

(58) Field of Classification Search
CPC ...... G06T 7/0012; G16H 50/20; A61B 5/0071
See application file for complete search history.

(56) References Cited

U.S. PATENT DOCUMENTS

| | | | | |
|---|---|---|---|---|
| 2019/0384048 A1* | 12/2019 | Valdes | .................. | G02B 21/36 |
| 2021/0117729 A1* | 4/2021 | Bharti | .................... | G06V 10/82 |
| 2021/0172931 A1* | 6/2021 | Larsen | .................. | G06T 7/0012 |
| 2021/0183034 A1* | 6/2021 | Chang | ................ | G01N 21/6456 |
| 2021/0256692 A1* | 8/2021 | Popescu | ................ | G06T 7/0012 |
| 2021/0321963 A1* | 10/2021 | Manor | .................... | G06T 11/00 |
| 2021/0325308 A1* | 10/2021 | Kannan | ............. | G01N 21/6458 |
| 2022/0036139 A1* | 2/2022 | Moore | .................. | G06T 7/0012 |

(Continued)

OTHER PUBLICATIONS

Colin L. Cooke et al.: "Physics-Enhanced Machine Learning for Virtual Fluorescence Microscopy", Apr. 21, 2020 (Year: 2020).*

(Continued)

*Primary Examiner* — David Bilodeau
(74) *Attorney, Agent, or Firm* — Honigman LLP; Brett A. Krueger (57) ABSTRACT

A computer-implemented method for predicting digital images in the form of a digital fluorescence representation together with a further derived representation by means of a combined machine learning system is described. The method comprises providing a first digital image of a tissue sample that was recorded under white light by means of a microsurgical optical system with a digital image recording unit, and predicting a second digital image of the tissue sample in a fluorescence representation and a further representation, which has optical indications about diseased tissue elements. This is done by means of a previously trained combined machine learning system comprising a trained combined machine learning model for predicting the second digital image of the tissue sample in the fluorescence representation and the further representation.

18 Claims, 6 Drawing Sheets

(56) References Cited

U.S. PATENT DOCUMENTS

| | | | |
|---|---|---|---|
| 2022/0084201 A1* | 3/2022 | Dai | G06N 3/045 |
| 2022/0358646 A1* | 11/2022 | Ryan | G06N 20/10 |
| 2022/0383986 A1* | 12/2022 | Popescu | G16H 30/40 |
| 2023/0030424 A1* | 2/2023 | Ozcan | G06F 18/24137 |
| 2023/0041229 A1* | 2/2023 | Tahvilian | G06T 7/90 |
| 2024/0029409 A1* | 1/2024 | Aidt | G06V 10/22 |
| 2024/0202923 A1* | 6/2024 | Saur | G06T 7/0012 |

OTHER PUBLICATIONS

Apr. 4, 2022 Office Action issued in corresponding German Application No. 10202111588.6.

Wieslander, Hakan et al. "Learning to see colours: generating biologically relevant fluorescent labels from bright-field images." bioRxiv, Jan. 27, 2021.

Nie, Shijie et al. "Deeply Learned Filter Response Functions for Hyperspectral Reconstruction," 2018 IEEE/CVF Conference on Computer Vision and Pattern Recognition, 2018, pp. 4767-4776, doi: 10.1109/CVPR.2018.00501.

Fabelo, Himar et al. "Deep Learning-Based Framework for In Vivo Identification of Glioblastoma Tumor using Hyperspectral Images of Human Brain." Sensors. 2019; 19(4):920.

\* cited by examiner

MULTI-TASK LEARNING OF WHITE LIGHT PHOTOGRAPHS FOR A SURGICAL MICROSCOPE

FIELD OF THE INVENTION

The invention relates to a method for predicting digital images in the form of a digital fluorescence representation and in particular to a computer-implemented method for predicting digital images in the form of a digital fluorescence representation together with a further derived representation by means of a combined machine learning system. The invention furthermore relates to a corresponding prediction system and computer program product.

TECHNICAL BACKGROUND

Brain tumours are a not infrequently occurring type of cancer that is comparatively aggressive and often has relatively low treatment success with a survival chance of approximately ⅓. Treatment of such diseases typically requires a surgical intervention for removal, radiotherapy and/or subsequent, usually lengthy, chemotherapy. Hitherto a biopsy has often formed the decision basis for the respective treatment, with molecular tests being able to be used as well. Of course, such interventions entail medical risks. The possibilities for analysing radiometrically recorded images have recently become very advanced and, as a result of this, such tumour examinations can at least complement biopsies. This may even be the case if biopsies are not possible or are undesirable. Recently these image-based diagnoses have even been able to be used during an operation. However, the required computing power is currently extremely high, which is why actual real-time support has not been possible hitherto.

It is not only in the field of brain tumours that diseased tissue regions have to be removed completely and as precisely as possible in order to prevent diseased tissue—i.e. tumour-containing tissue—from growing into healthy tissue again, and in order to retain as much healthy tissue as possible. This partial removal of tissue (resection) is normally carried out by a surgeon in an operating theatre equipped with special instruments. A surgical microscope (OPMI) is also generally used for this purpose. In this case, the exact boundary line between healthy and cancerous tissue is recognizable only with difficulty under the typical white operation light. As a result, there is clearly the risk of too much healthy tissue or too little cancerous tissue having been removed after the resection. Both results may be designated as suboptimal.

Hitherto it has generally been necessary, moreover, to inject a contrast agent several hours before the operation, in order to differentiate relatively clearly between healthy and diseased tissue under optimized lighting (e.g. BLUE400 or YELLOW560). As a result, it may also be necessary to have to switch between lighting presettings relatively frequently during the operation. Both circumstances contribute to longer preparation and operation times, overall higher operation costs and less patient-friendliness.

The prior art does indeed disclose initial approaches for using artificial intelligence to ascertain a fluorescence image from a tissue recording that was recorded under white light. Nevertheless, high-resolution cameras having a multiplicity of colour channels are required for this purpose.

It would thus be desirable to have minimally invasive operation support that helps the surgeon, in real time—i.e. without a significant time delay—and without great distraction of attention, to differentiate unambiguously between healthy and cancerous tissue in order that the patients are thus subjected only to minor additional treatments (e.g. chemotherapy).

Overview of the Invention

This object is achieved by means of the method proposed here, the corresponding system and the associated computer program product in accordance with the independent claims. Further embodiments are described by the respective dependent claims.

In accordance with a first aspect of the present invention, a computer-implemented method for predicting digital images in the form of a digital fluorescence representation together with a further derived representation by means of a combined machine learning system is presented. In this case, the method comprises providing a first digital image of a tissue sample that was recorded under white light by means of a microsurgical optical system with a digital image recording unit, and predicting a second digital image of the tissue sample in a fluorescence representation and a further representation, which gives optical indications about diseased tissue elements. This can be effected by means of a previously trained combined machine learning system comprising a trained combined machine learning model for predicting the second digital image of the tissue sample in the fluorescence representation and the further representation.

In accordance with a further aspect of the present invention, a prediction system for predicting digital images in the form of a digital fluorescence representation together with a further derived representation by means of a combined machine learning system is presented. The prediction system comprises a memory that stores program code and one or more processors that are connected to the memory and that, when they execute the program code, cause the prediction system to control the following units of the prediction system: (i) a microsurgical optical system with a digital image recording unit for providing a first digital image of a tissue sample that was recorded under white light, and (ii) a prediction module for predicting a second digital image of the tissue sample in a fluorescence representation and a further representation, which gives optical indications about diseased tissue elements. This can be done by means of a previously trained combined machine learning system comprising a trained combined machine learning model for predicting the second digital image of the tissue sample in the fluorescence representation and the further representation.

The proposed computer-implemented method for predicting digital images in the form of a digital fluorescence representation together with a further derived representation by means of a combined machine learning system has a number of advantages and technical effects, which may also apply, mutatis mutandis, to the associated system:

The proposed concept allows an elegant solution to at least four requirements: What is made possible in the context of tumour analysis is that the type and the severity of the existing tumour that is currently in the field of view of the surgical microscope are carefully classified by way of additional representations. This can also be regarded as a second opinion in addition to that of the surgeon. In this case, the proposed concept proves to be advantageous insofar as experience shows that neurosurgeons are often not certain when determining the tumour type.

Furthermore, the proposed method allows optical highlighting of possible regions to be removed by way of the representation of a correct segmentation mask that can be made optically visible together with the fluorescence representation. As a result, a virtual guidance of the operation on the part of the surgeon is made possible, and it is also possible to generate warnings in the event of an inadvertent change into supposedly healthy tissue.

The visualization used in this case enables the surgeon to differentiate unambiguously between healthy and diseased tissue. Moreover, the proposed method and the associated system are robust and require only a comparatively small number of training data since only one cohesive or combined machine learning system has to be trained.

It is true that rudimentary partial solutions exist both for a fluorescence representation derivation of a recording of partly diseased tissue and for a subsequent, temporally downstream and separate segmentation from an already existing fluorescence representation. However, this separate image processing has proved not to be particularly practical. This is owing to the fact, inter alia, that first of all two completely different machine learning models have to be designed and trained. In productive use these models would require a double loading of the available computation resources (in particular processor and memory). Moreover, the I/O channels would also be significantly loaded by the generation of output data of the first model and renewed reading—in as input data for a second model.

Besides separate storage of the two machine learning models, these models would also have to be separately developed, maintained, versioned and continually correlated relative to one another in the event of a change in one of the two models.

Besides these purely technical disadvantages, a series of algorithm disadvantages arise, too, which are clearly overcome by the system proposed here. Even a combination of known techniques in order to generate a fluorescence representation and also a segmentation view would not enable direct support of a surgeon during an operation since none of the methods known hitherto has a real-time capability. Moreover, the different models would first have to be trained independently of one another, which would constitute a multiple outlay for the provision of the training data and the necessary annotations. Furthermore, it should always be assumed that, if output data of one machine learning system are used as input data for another machine learning system, non-negligible data gaps would arise.

As a result of the joint generation—i.e. prediction—of the fluorescence representation and a segmentation with regard to a demarcation between healthy and diseased tissue—either derived from one another or in parallel—the surgeon is also enabled to assess the machine-generated segmentation into healthy and diseased tissue from a represented fluorescence representation. Direct quality control of the representations generated by the method in real time during the operation becomes possible in this way.

In summary, the advantages of the single-stage method can thus be presented as follows: Firstly, fewer training data are required in order to optimize all the parameters of the combined machine learning system, and a plurality of tasks can be "learned" in combination (multitask learning). The differences between the predictions and the ground truth data can be reduced to deviation errors that do not influence, or that influence only insignificantly, the respective other type of representation (e.g. fluorescence representation, segmentation).

Classification and segmentation results can be generated pixel by pixel from the corresponding images that were recorded using visible light (VIS) and the fluorescence representation (SLS). This would not be possible in the case of pure segmentation models since the representations under UV light (SLS) would normally have been recorded at different times since it would firstly be necessary to enhance the tissue sample using contrast agent.

Moreover, the training becomes more reliable in comparison with a direct prediction of segmentation representations from a white light recording because the virtual "tile prediction" can be regarded as a virtual intermediate task.

From the standpoint of multitask learning it should also be mentioned that in the case of traditional pure prediction of a fluorescence image (VIS) from a digital image that was recorded under visible light (SLS), without a further representation being predicted additionally and simultaneously, important items of information could be lost or would be discarded since they are not pertinent to the prediction of the fluorescence image. In contrast thereto, in the case of the coupled prediction proposed here "VIS image→SLS image→additional representation/optical highlighting" for the optical highlighting of potentially diseased tissue elements, the items of information from the generation (or prediction) of the SLS representation that are discarded (since they are not relevant) as part of traditional approaches are also used for the prediction of the optical highlighting, thus resulting in a clear advantage over traditional methods.

Further exemplary embodiments are presented below, which can have validity both in association with the method and in association with the corresponding system.

In accordance with one advantageous embodiment of the method, the digital image recording unit can process three or four colour channels—or alternatively even more. This would have the advantage that a commercially available camera unit—e.g. an RGB camera—could also be utilized in productive use of the method and/or the system. Such devices are available with moderate through to high-resolution characteristics. Alternatively, the use of one or more monochrome cameras-optionally equipped with filters—would also be possible.

In accordance with a further advantageous embodiment of the method, the trained combined machine learning model can predict both the second digital image in the fluorescence representation and simultaneously the further representation in the form of at least one optical highlighting. This parallelism of the predictions of different representations—i.e. the fluorescence representation and also the further representation with the at least one optical highlighting-affords a significant increase in speed compared with methods known hitherto, which proceed sequentially. The optical highlighting could also be displayed jointly with the fluorescence representation on a visual display unit, by the two representations being displayed in an overlapping fashion. In this way, diseased tissue can be made visible directly in the fluorescence representation, e.g. by way of a different colour representation, a segmentation or by way of a demarcation line.

Accordingly and in accordance with another interesting embodiment of the method, the predicted digital second image in the fluorescence representation and the predicted optical highlighting can be represented within one view—i.e. in one image as just described.

In accordance with one supplementary embodiment of the method, the further representation can be produced from the fluorescence representation of the predicted second digital image by the trained combined learning system too. As a result, computer resources could potentially be saved, although this could possibly result in a lengthening of the prediction time. By virtue of the fact that both variants—i.e. the parallel version described further above and the sequential version described here—are possible, the concept proposed in the context of this document proves to be exceptionally flexible.

In accordance with another supplementary embodiment of the method, the further representation can be a third digital image. The latter can firstly also be represented independently of the predicted second digital image. Thus, as a result of the flexible possibilities that are able to be realized by way of the proposed method, a surgeon would have excellent possibilities for variation of the representation of the different predicted formats. Since the further representation can also show a classification of a possible disease or else the severity thereof, the second representation could also be effected in an alphanumeric form or some other graphical form. In this case, a separation of the predicted second and third digital images on different display units may prove to be entirely expedient.

In accordance with one elegant embodiment of the method, the learning model can correspond to an encoder-decoder model or a classification network—e.g. in the form of a deep neural network—in terms of its set-up. Both the first alternative mentioned and the second can be used for classification tasks. The result of the classification that would be visualized in accordance with the second representation can relate to a health grade—e.g. "healthy", "slight severity", "medium severity", "high severity"—or to a disease type—e.g. type X, type Y, type Z, type C. Besides a textual representation, this could also be elegantly represented graphically.

In accordance with a further embodiment of the method, the encoder-decoder model can be a convolutional network in the form of a U-net. This architecture allows fast processing of recordings of biological tissue samples and moreover requires comparatively few training data.

In accordance with a further developed embodiment of the method, training the combined machine learning system can comprise the following: (i) providing a plurality of first digital training images of tissue samples—e.g. brain tissue, cancer tissue, etc.—that were recorded under white light by means of a microsurgical optical system—i.e. e.g. a surgical microscope—with a digital image recording unit—i.e. for example a camera. These recordings may also have been produced asynchronously—i.e. earlier—with respect to the actual implementation of the actual training of the machine learning system.

Furthermore, this embodiment can comprise providing a plurality of second digital training images in a fluorescence representation, which represent the same tissue samples as the first set of digital training images. In this case, the second digital training images can additionally have metainformation. This can involve annotations that may specify what is expected from the machine learning system as the result once the training phase has been concluded. Said metainformation can consist of a pixel-by-pixel annotation of diseased tissue pixels, can be a border of diseased tissue, or diseased tissue can be represented in a different colour; in principle, any type of segmentation is permissible.

Finally, this part of the method according to the invention can comprise training—in particular "supervised learning"—of the combined machine learning system for forming the combined machine learning model for predicting the second digital image—i.e. the fluorescence representation—and the further representation. In this case, the following can be used as input parameters for the combined machine learning system: (i) the plurality of first digital training images, and (ii) the plurality of second digital training images as ground truth, i.e. target output values that the machine learning system is intended to output in this or a similar way if unknown input data are received during the prediction phase.

The two types of training data allow a parallel optimization of the combined machine learning model of the machine learning system with regard to the fluorescence representation and the further representation. It is not necessary for the additional representation to be derived from the fluorescence representation. Such sequential processes are generally slower and less accurate because data losses arise between the part of a sequential method. This can be elegantly prevented in the manner proposed here.

In accordance with a further embodiment of the method, the fluorescence representation of each of the plurality of second digital training images can be obtained by employing a contrast agent in the corresponding tissue samples and illuminating with light of a predetermined wavelength. By way of example, the known BLUE 400 (in the UV range), YELLOW 560 or INFRARED 800 (in the infrared range) is used as predetermined wavelength.

In accordance with one advantageous embodiment of the training part of the method, the additional metainformation in the second set of digital training images that indicates diseased tissue elements can consist of at least one optical highlighting of the diseased tissue elements. This can involve, in principle, the same types of highlightings as have already been described further above for the prediction phase (e.g. pixel-by pixel annotating, framing, colour contrasting or segmenting in some other way).

In accordance with a further developed embodiment of the method, the additional metainformation in the second set of digital training images that indicates diseased tissue elements can be a predicted class—i.e. classified—of a tumour grade. The surgeon would thus obtain indicators of the severity of the disease directly during the operation. In order to make that possible, these conditions should also be supported during training with training images or other metainformation.

In accordance with a still further developed embodiment of the method, the additional metainformation about diseased tissue elements in the second digital training images can be separate third digital training images. This would be integrable seamlessly in the training process and would provide good support of an optimization of the parameter values of the machine learning system.

Furthermore, embodiments can relate to a computer program product able to be accessed from a computer-usable or computer-readable medium that comprises program code for use by, or in conjunction with, a computer or other instruction processing systems. In the context of this description, a computer-usable or computer-readable medium can be any device that is suitable for storing, communicating, transferring, or transporting the program code.

OVERVIEW OF THE FIGURES

It should be pointed out that exemplary embodiments of the invention may be described with reference to different implementation categories. In particular, some exemplary embodiments are described with reference to a method, whereas other exemplary embodiments may be described in the context of corresponding devices. Regardless of this, it is possible for a person skilled in the art to identify and to combine possible combinations of the features of the method and also possible combinations of features with the corresponding system from the description above and below-if not specified otherwise-even if these belong to different claim categories.

Aspects already described above and additional aspects of the present invention become apparent inter alia from the exemplary embodiments that are described and from the additional further specific embodiments described with reference to the figures.

Preferred exemplary embodiments of the present invention are described by way of example and with reference to the following figures.

DETAILED DESCRIPTION OF THE FIGURES

In the context of this description, conventions, terms and/or expressions should be understood as follows:

The term "machine learning system" here may describe a system or else a method which is used to generate output values in a non-procedurally programmed manner. For this purpose, in the case of supervised learning, a machine learning model present in the machine learning system is trained with training data and associated desired output values (annotated data or ground truth data). The training phase may be followed by the productive phase, i.e. the prediction phase, while the output values are generated/predicted from previously unknown input values in a non-procedural manner. A large number of different architectures for machine learning systems are known to the person skilled in the art. They include neural networks, too, which can be trained and used as a classifier, for example. During the training phase, the desired output values given predefined input values are typically learned by means of a method called "backpropagation", wherein parameter values of nodes of the neural network or connections between the nodes are automatically adapted. In this way the machine learning model inherently present is adjusted or trained in order to form the trained machine learning system with the trained machine learning model.

The term "prediction", in line with the discussion above, may describe the phase of productive use of a machine learning system. During the prediction phase of the machine learning system, output values are generated or predicted on the basis of the trained machine learning model, to which previously unknown input data are made available.

The term "combined machine learning system" here describes a combination of at least two machine learning systems which are coupled to one another or machine learning systems which are integrated in one another and which outwardly appear as a homogeneous machine learning system adapted to generate or predict more than one type of output data. These output data may be, for example, firstly a digital fluorescence image and secondly a corresponding segmentation or classification.

The term "combined machine learning system" here describes a combination of at least two machine learning systems which are coupled to one another or are integrated in one another and which outwardly appear as a homogeneous machine learning system adapted to generate or predict more than one type of output data. These output data may be, for example, firstly a digital fluorescence image and secondly a corresponding segmentation or classification.

In customary machine learning systems, training typically concentrates on optimizing the machine learning model with regard to a parameter to be learned. However, it can happen in this case that similarly formulated tasks are disregarded in this case, and valuable information is dispensed with or ignored. In this case, however, precisely the fluorescence representation and the further representation-particularly if a prediction for a tumour type or indications concerning the tumour severity is involved—can provide expedient supplementation. An expedient supplementation on the training data side-particularly in the case of the annotation data or ground truth data-would be extremely efficient for this purpose. What can thus be achieved overall is that the machine learning model thus trained generalizes better in comparison with a singular task. This may be referred to as multitask learning, for which two loss functions (for the case of two parallel predictions) are utilized during learning for optimization purposes.

Since the training data normally all have data noise, multitask learning acts indirectly as an enlargement of the amount of training data. This is owing to the following: If the learning model is trained with regard to a task A, normally all side aspects, i.e. including the noise, are ignored. However, since different tasks have varying noise patterns, it becomes possible for a better generalization to be achieved by way of the simultaneous learning/training of/with regard to two tasks. Training oriented only towards task A may lead to undesirable overfitting, while joint training for tasks A and B enables a machine learning model since averaging is effected with regard to the varying data noise for the two tasks. Therefore, this has the same effects as an enlarged amount of training data since the machine learning models mutually support one another with regard to the double optimization and a very effective combined machine learning system can thus be made possible by means of multitask learning.

The term "further derived representation" describes here-besides the digital fluorescence image-a further form of output data of the machine learning system, wherein the further derived representation can assume various forms. Examples thereof are a segmentation view that subdivides the input image into healthy and diseased tissue regions, or else text-based outputs such as, for example, the severity of the tumour disease of the diseased tissue or the tumour type itself. Besides the aforementioned text-based output, corresponding output data can also be represented graphically. Furthermore, it is possible to represent the digital fluorescence image and the further derived representation in an overlapping fashion. In this case, it is unimportant whether the further derived representation is derived from the already predicted fluorescence image or is generated or predicted from the first digital image, which is used as input data for the machine learning system, directly in the context of the prediction process of the machine learning system.

The term "digital images" here describes a data set of pixels that was recorded by a digital recording device—e.g. a digital camera.

The term "digital fluorescence representation" here describes a view of a digital image that corresponds to the view that would arise if a tissue sample provided with contrast agent were illuminated with light of a specific wavelength—e.g. UV light.

The term "first digital image" here describes an image of biological tissue recorded by a digital recording device, e.g. a mixture of healthy and diseased tissue. The tissue can be brain tissue recorded by means of a surgical microscope during a surgical intervention.

The term "tissue sample" describes the mixture of healthy and diseased tissue already mentioned.

The term "microsurgical optical system" here describes for example a surgical microscope equipped with an electronic recording device (i.e. camera).

In the context of this document, the term "digital image recording unit" describes an electronic camera equipped for example with 3 to 4 colour channels. One or a plurality of monochrome electronic cameras are furthermore conceivable.

The term "second digital image" here describes output data of the machine learning system during the prediction phase, in particular the digital fluorescence image.

The term "encoder-decoder model" here describes an architecture of a machine learning system in which input data are encoded or coded in order then to be decoded again immediately afterwards. In the middle between the encoder and the decoder the necessary data are present as a type of feature vector. During decoding, depending on the training of the machine learning model, specific features in the input data can then be specially highlighted.

The term "classification network" here describes a form of machine network or neural network which can classify a set of input data into specific classes as output data.

The term "U-net" here describes an architecture of a machine learning system which is based on a convolutional network architecture. This architecture is particularly well suited to a fast and accurate segmentation of digital images in the biological/medical field. A further advantage of such a machine learning system is that it manages with fewer training data and allows a comparatively accurate segmentation.

The term "first digital training images" here describes a digital image of biological tissue that is recorded by means of a surgical microscope, for example.

The term "second digital training images" here describes a digital image that is expected as a result of a prediction if the first digital training image is predefined for the machine learning system. In this respect, the second digital training image can be regarded as ground truth information during the training phase of the machine learning system.

The term "metainformation" here describes information that is additionally present in a second digital training image or is linked thereto. This can involve pixel-by-pixel annotations indicating areas of diseased tissue regions, or else a tumour type or a severity of the disease of specific tissue regions. Further types of metainformation can be supplemented, which can also be represented as an optical indication and can also be present in the form of a further digital training image. The latter should ideally image the same region of the tissue sample as the first digital training image.

The term "ground truth" or ground truth data describes the expected output data of a machine learning system that are fed to a machine learning system in the training phase besides the actual input data in order to adapt or optimize parameter values of the machine learning system—for example nodes and their interconnections in the case of a neural network.

A detailed description of the figures is given below. It is understood in this case that all of the details and information in the figures are illustrated schematically. Firstly, a flowchart-like illustration of one exemplary embodiment of the computer-implemented method according to the invention for predicting digital images in the form of a digital fluorescence representation together with a further derived representation by means of a combined machine learning system is presented. Further exemplary embodiments, or exemplary embodiments for the corresponding system, are described below.

Figure 1:
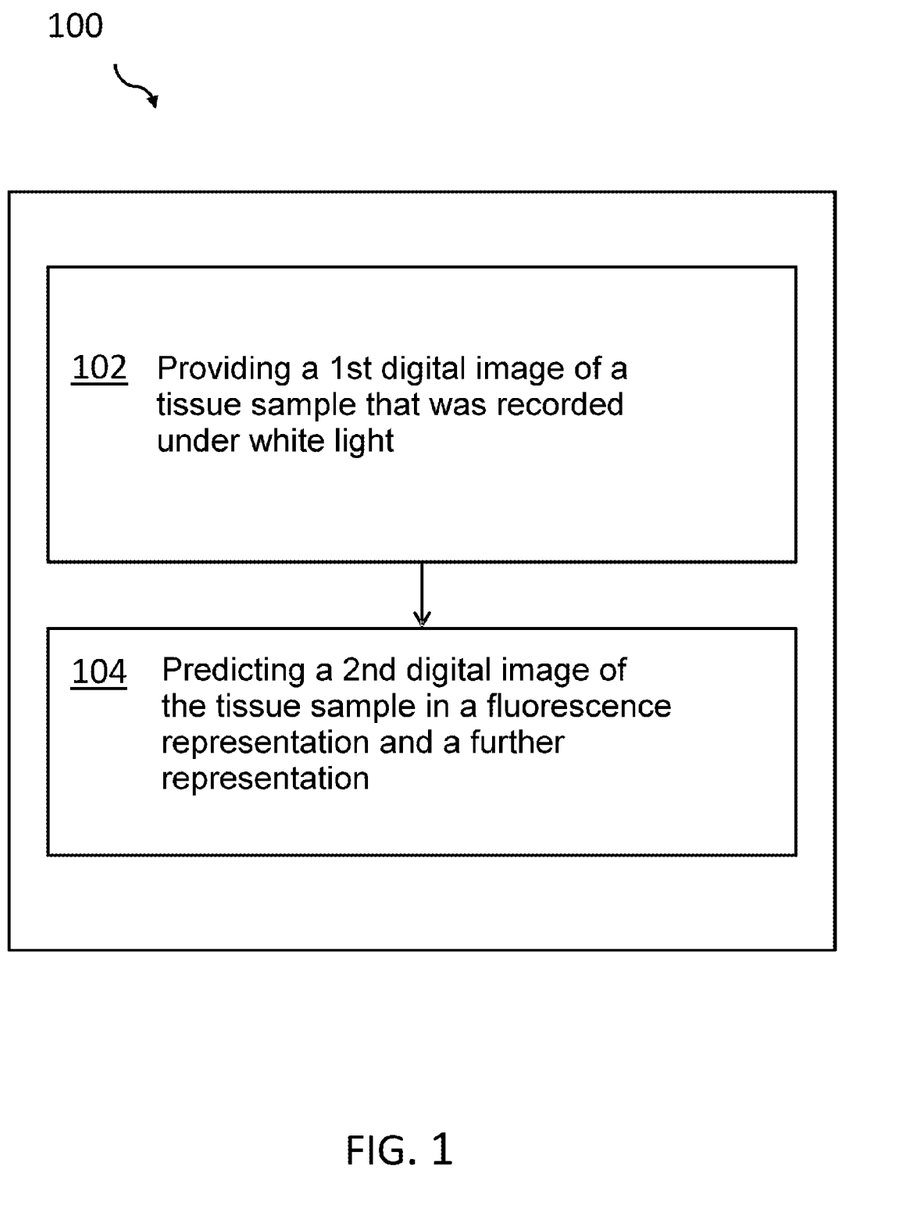
FIG. 1 presents a flowchart-like illustration of one exemplary embodiment of the computer-implemented method according to the invention for predicting digital images in the form of a digital fluorescence representation together with a further derived representation by means of a combined machine learning system.

FIG. 1 presents a flowchart-like illustration of one preferred exemplary embodiment of the computer-implemented method 100 for predicting digital images in the form of a digital fluorescence representation together with a further derived representation by means of a combined machine learning system. The method comprises providing 102 a first digital image of a tissue sample that was recorded under white light (VIS—visible light source) by means of a microsurgical optical system—in particular by means of a surgical microscope with a digital image recording unit—i.e. a digital camera that processes for example 3-4 colour channels. It should be noted here that said first digital image is passed to the machine learning system directly and immediately after the image recording, or that there is an intervening period of time. A significantly improved support of real operations would be afforded in the first case, while the second scenario could be used better for research projects.

Furthermore, the method 100 comprises predicting 104 a second digital image of the tissue sample—in particular of the same tissue sample—in a fluorescence representation and a further representation, which gives optical indications about diseased tissue elements. This is done by means of a previously trained combined machine learning system comprising a trained combined machine learning model for predicting both the second digital image of the tissue sample in the fluorescence representation and the further representation.

Figure 2:
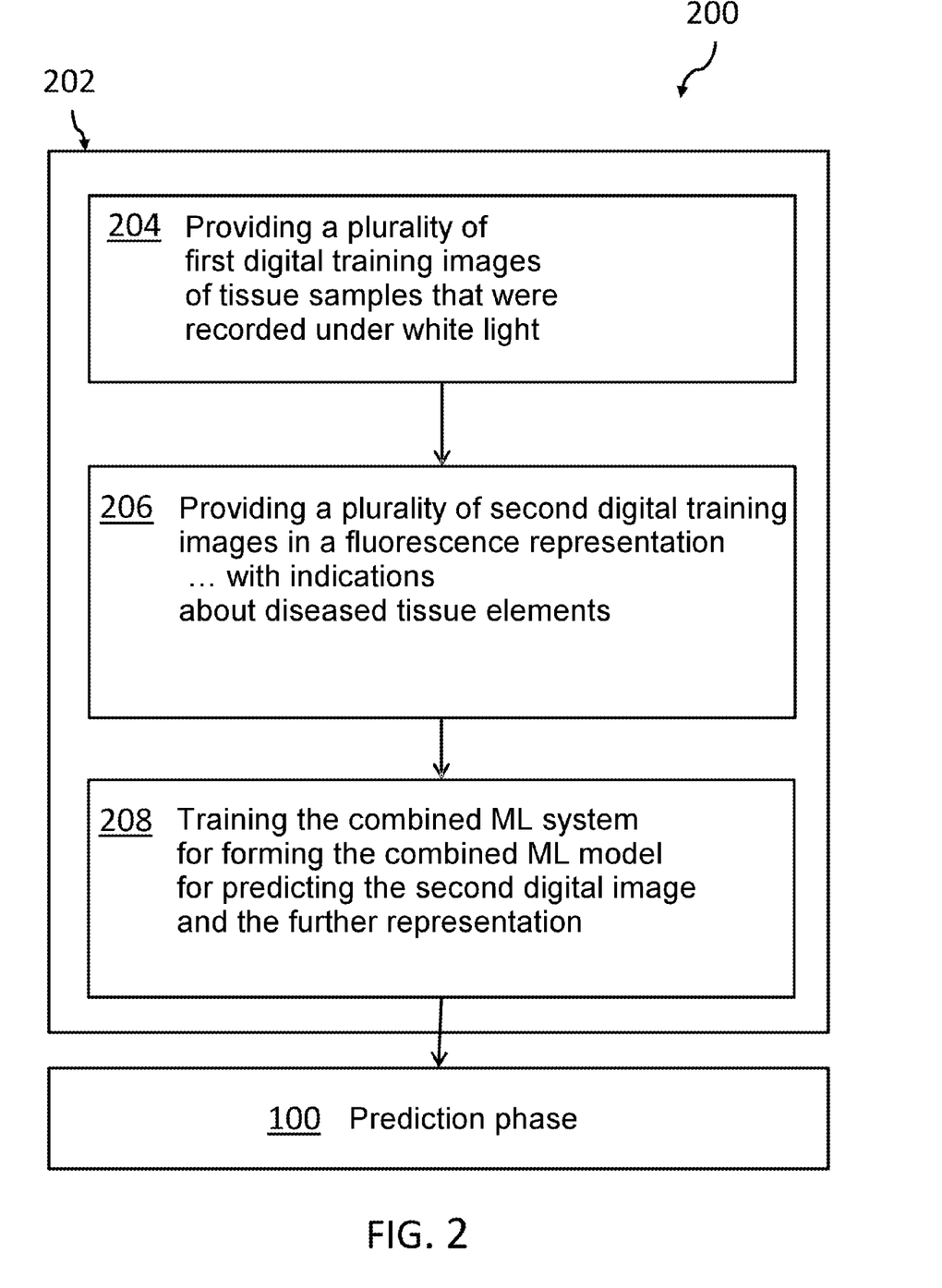
FIG. 2 shows a flowchart-like illustration of an extended exemplary embodiment of the method in accordance with FIG. 1.

FIG. 2 shows a flowchart-like illustration of an extended exemplary embodiment 200 of the method in accordance with FIG. 1. This describes the training phase 202 for the prediction phase 100 of the method. In this case, training the combined machine learning system comprises providing 204 a plurality of first digital training images of tissue samples that were recorded under white light by means of a microsurgical optical system with a digital image recording unit, and providing 206 a plurality of second digital training images in a fluorescence representation, which represent the same tissue samples as the first set of digital training images. In this case, the second digital training images additionally have metainformation about diseased tissue elements. There additionally follows the actual process of training 208 the combined machine learning system for forming the combined machine learning model for predicting the second digital image and the further representation. In this case, the following variables are used as input parameters for the combined machine learning system: (i) the plurality of first digital training images, and at least (ii) the plurality of second digital training images as ground truth data. In this case, the training also uses further input data used in the form of indications about diseased tissue elements in the plurality of second digital training images as additional ground truth data.

Figure 3:
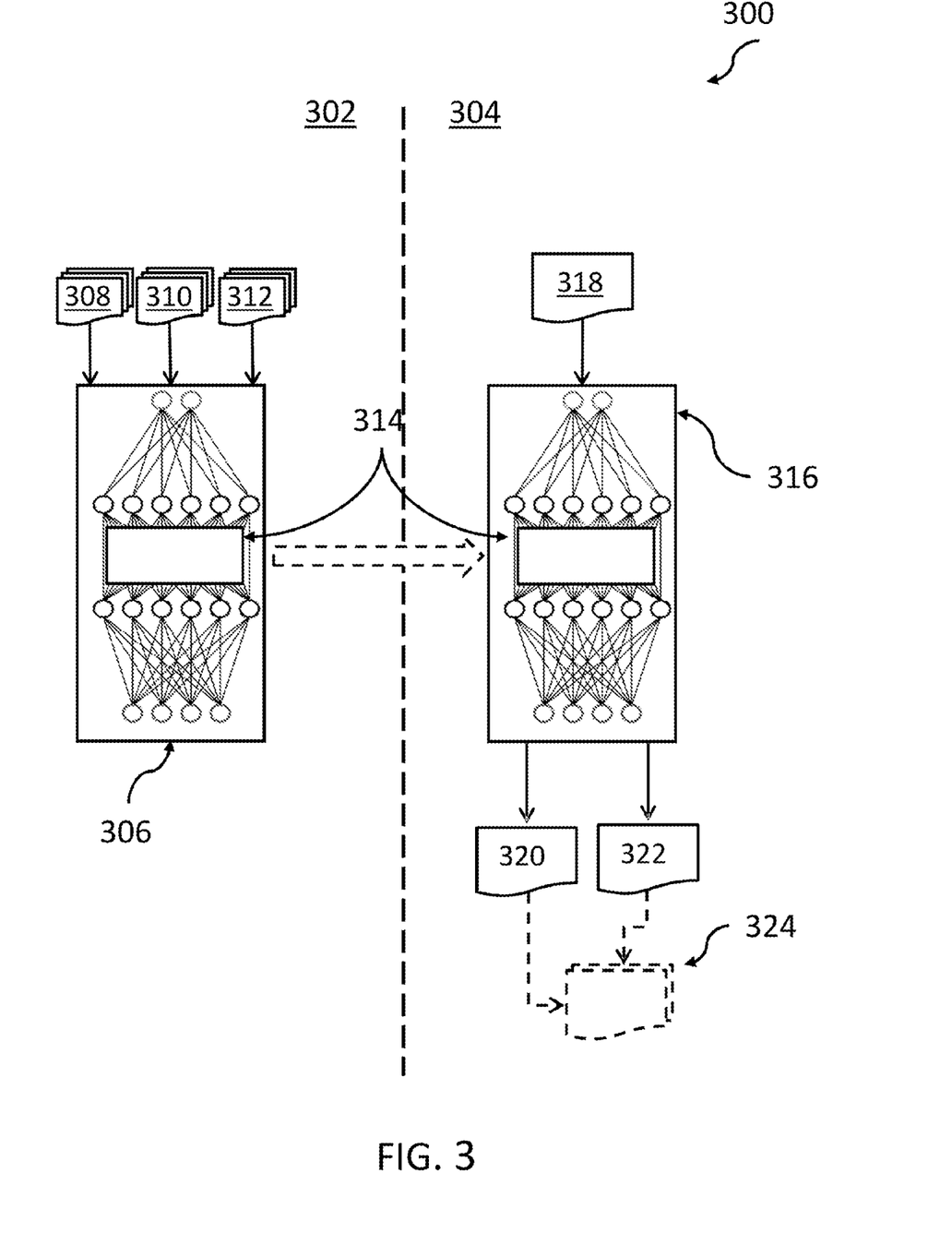
FIG. 3 shows the machine learning system in the training phase and in the prediction phase.

FIG. 3 shows as one example embodiment the machine learning system in the training phase 302 and in the prediction phase 304. The two phases are separated from one another by the vertical dashed line in the middle of the figure. The illustration of the machine learning system 306 is merely a symbolic depiction and should not suggest a specific type of a machine learning system. A workflow for generating training data could be manifested as follows: There ideally exist tuples of digital images having corresponding instances of the white light recordings and all derived representations. Examples of the derived representations—i.e. further representations-would be a fluorescence representation, a segmentation representation, an indication concerning the tumour type and an indication concerning the tumour severity.

Optionally, a plurality of data sets without complete tuples can also be used. In this case, it is also possible to use only subsets of data of ideally derived or further representations. Data of such subsets would be used only for the optimization of a particular machine learning submodel during training. Examples would be a first data set having correspondingly a white light recording of the tissue and a corresponding fluorescence representation. A second data set could contain a white light recording, a tumour type and a tumour severity. A third data set could contain the white light recording (or white light representation) of the tissue, the associated fluorescence representation, the tumour type and a segmentation representation.

An areal alignment of the white light recordings, corresponding fluorescence representations and also corresponding segmentation representations is desirable in any case.

Data selection and data preparation can optionally also include removal of digital images having severe limitations such as severe colour casts and/or partial reflections. Furthermore, it is optionally possible to perform a two-dimensional alignment of white light recordings and fluorescence representations that are temporally separated from one another by a short intervening period, in order thus to form a further data set. In addition, logarithmic transformations of digital images can be performed in order to counteract excessively strong fluorescence signals at the trailing end.

In the supplementary technical field of "data augmentation", it is also possible to provide a spatial simulation (two-dimensional) of further training images by way of a left/right mirroring, top/bottom mirroring, random rotation, random cropping, etc. This can be used if there is an imbalance with regard to training images in respect of the fluorescence level. In this case, training images in under-represented fluorescence groups can be multiply copied in order to correspond to the number of training data in the fluorescence groups that are best equipped with examples.

Accordingly, a first set of digital training images 308 that correspond to the white light recordings is used as training data. Furthermore, a second set of digital training images 310 is used as ground truth data for the training. Said second set of digital training images can contain additional indications about diseased tissue regions. The latter are illustrated in the figure as an additional representation or as a third set of digital training images 312. Consequently, a respective tuple composed of corresponding digital images of the first set of digital training images 308, the second set of digital training images 310 and the third set of digital training images 312 forms in each case a data set that refers to the same digital image of the first set of training images 308. In this case, the third set of digital training images can also assume the form of a vector—or even the form of a scalar value or alphanumeric value—that refers to the severity of the tumour or to the tumour type.

After completion of the training of the machine learning system 306 with the machine learning model 314, the machine learning model 314 now belonging to the trained combined machine learning system 316 can be used productively in the prediction phase 304. As input data for the trained combined machine learning system 316, now-potentially in real time-white light recordings 318 (first xxx originating from a digital recording unit (e.g. a digital camera) are used, such that firstly a corresponding fluorescence image 320 (digital image in a fluorescence representation) and secondly the other representation 322 (severity of the disease, tumour type, segmentation, etc.) can be output. Both representations 320, 322 can be integrated in one another either as picture—in-picture representation or as 100% overlap (or partial overlap). In the case of segmentation—i.e. an optical highlighting of the diseased tissue—the diseased tissue would be represented with a different colour, for example. This gives the surgeon—in particular a less experienced surgeon-clear indications of the line along which diseased tissue can be separated from non-diseased tissue.

Figure 4:
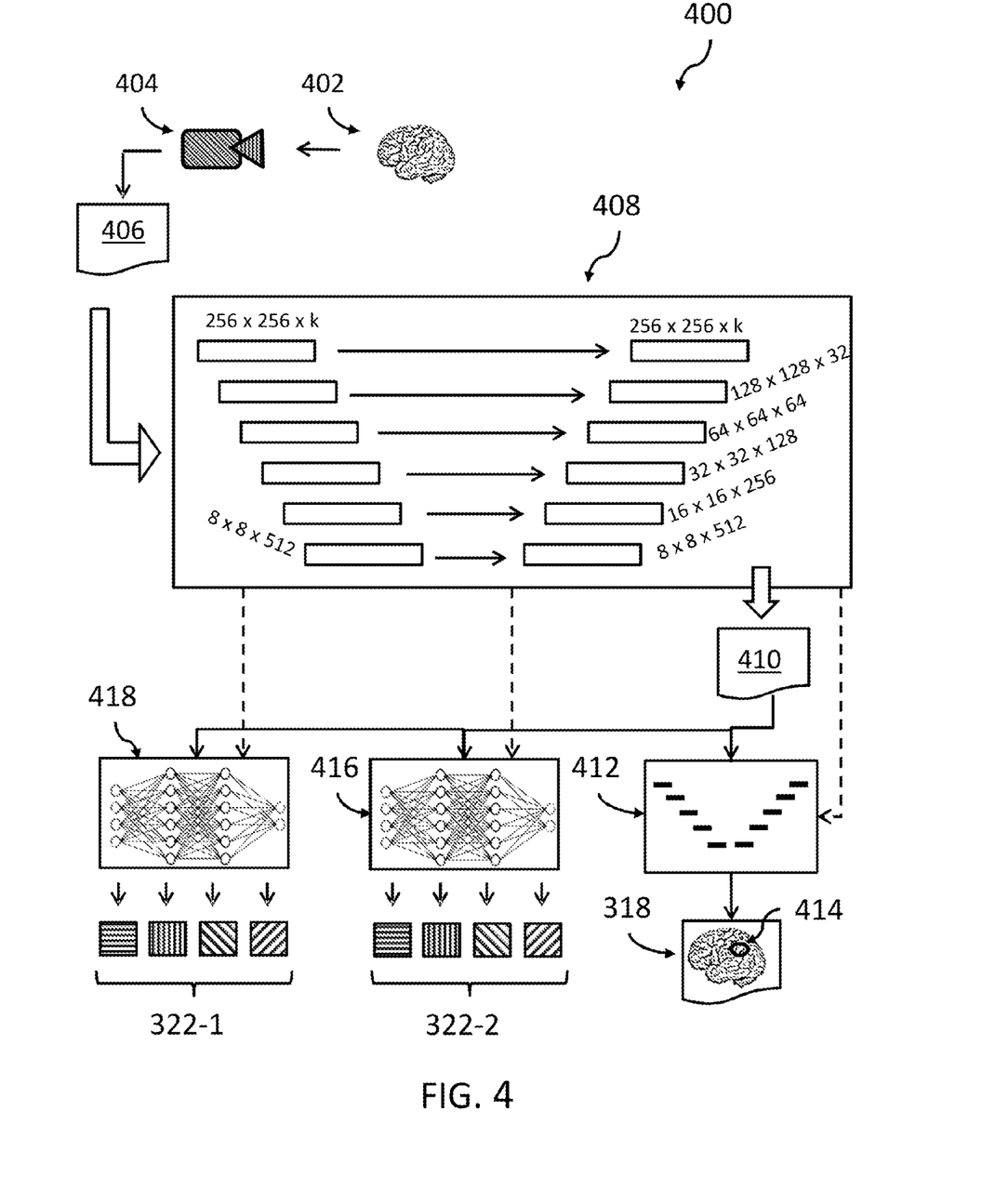
FIG. 4 shows one exemplary embodiment of the prediction system including various parts of the combined machine learning system.

FIG. 4 shows one exemplary embodiment 400 of the prediction system including various parts of the combined machine learning system. Firstly, a white light recording 406 of the tissue 402 is recorded by a digital recording unit 404. Said recording is used as input data for the machine learning system 408. The latter can have the architecture of a U-net—as illustrated. The fluorescence image 410 is then generated (i.e. predicted) as output data. Either directly in parallel or subsequently (dashed line from U-net 408 to the U-net 412), segmentation data 414 can then be predicted, which are representable in an overlapping representation 324 (cf. FIG. 3, 324). In addition, further representations, for example in the form of the indication of a severity 322-2 or a tumour type 322-1 would be possible either in direct coupling between parts of the machine learning system 408, 412 and also 416 and 418 (cf. dashed lines illustrated). The learning (sub) systems 416 and 418 can assume the form of neural classification networks—such as e.g. VGG (a particularly powerful convolutional neural network from the Visual Geometry Group at the University of Oxford) or Resnet (Residual Network).

Figure 5:
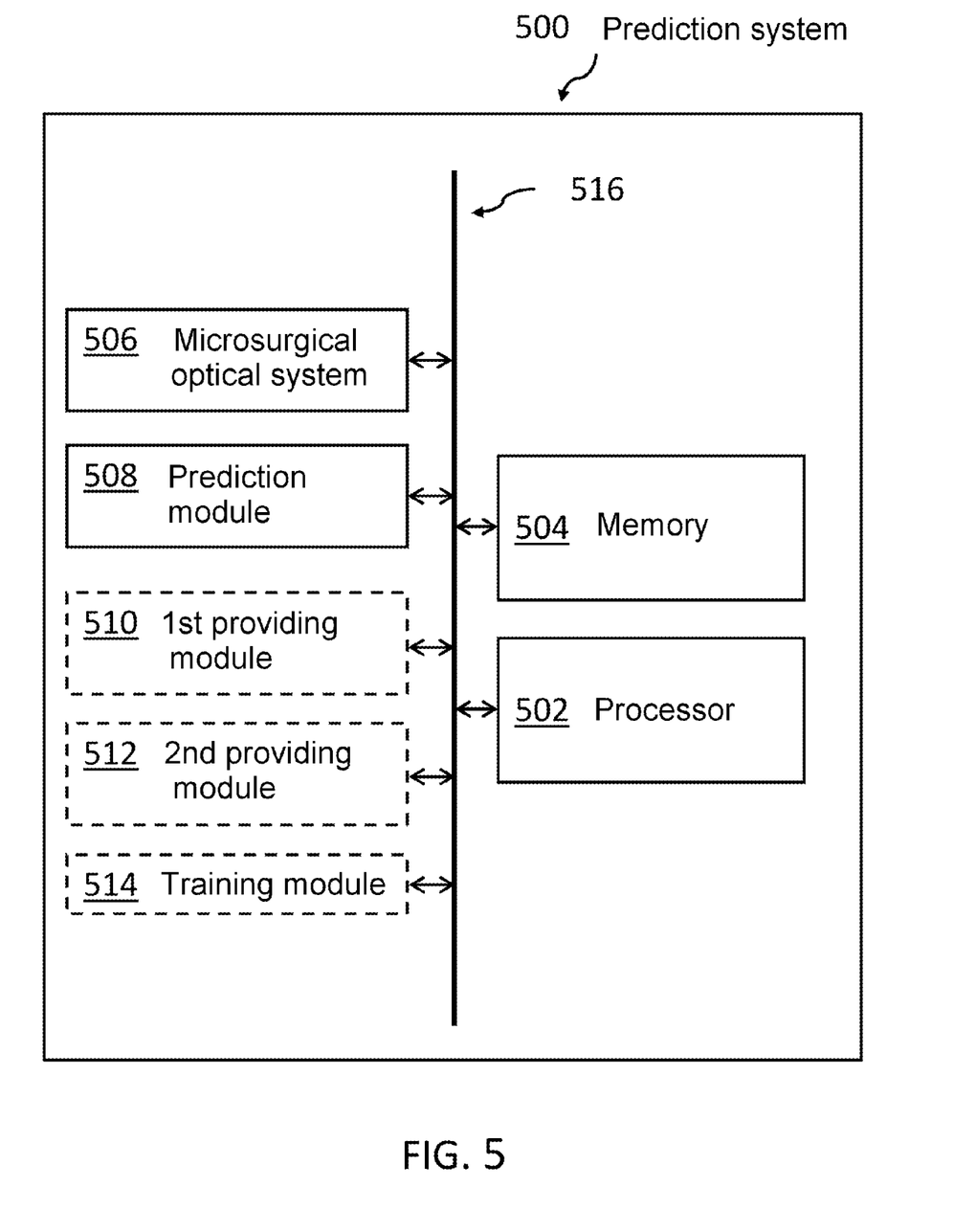
FIG. 5 shows one exemplary embodiment of the prediction system for predicting digital images in the form of a digital fluorescence representation together with a further derived representation by means of a combined machine learning system.

For the sake of completeness, FIG. 5 shows one exemplary embodiment of the prediction system 500 for predicting digital images in the form of a digital fluorescence representation together with a further derived representation by means of a combined machine learning system. The prediction system comprises a memory 502 that stores program code and one or more processors 504 that are connected to the memory 502 and that, when they execute the program code, cause the prediction system 500 to control the following units: (i) a microsurgical optical system 506 with a digital image recording unit—e.g. a surgical microscope with a camera—for providing a first digital image of a tissue sample that was recorded under white light, and (ii) a prediction module 508 for predicting a second digital image of the tissue sample in a fluorescence representation and a further representation, which have optical indications about diseased tissue elements, by means of a previously trained combined machine learning system comprising a trained combined machine learning model for predicting the second digital image of the tissue sample in the fluorescence representation and the further representation.

Optionally, the prediction system for the training phase can comprise further modules: (iii) a first providing module 510 for providing a plurality of first digital training images of tissue samples that were recorded under white light by means of a microsurgical optical system with a digital image recording unit, (iv) a second providing module 512 for providing a plurality of second digital training images in a fluorescence representation, which represent the same tissue samples as the first set of digital training images, wherein the second digital training images additionally have metainformation about diseased tissue elements, and (v) a training module 514 for training the combined machine learning system for forming the combined machine learning model for predicting the second digital image and the further representation. In this case, the following are used as input parameters for the combined machine learning system: (a) the plurality of first digital training images, and (b) the plurality of second digital training images as ground truth data.

It should expressly be pointed out that the modules and units—in particular the processor 502, the memory 504, the microsurgical optical system 506, the prediction module 508 and also the 1st providing module 510, the 2nd providing module 510 and the training module—can be connected to electrical signal lines or via a system—internal bus system 516 for the purpose of signal or data exchange.

Figure 6:
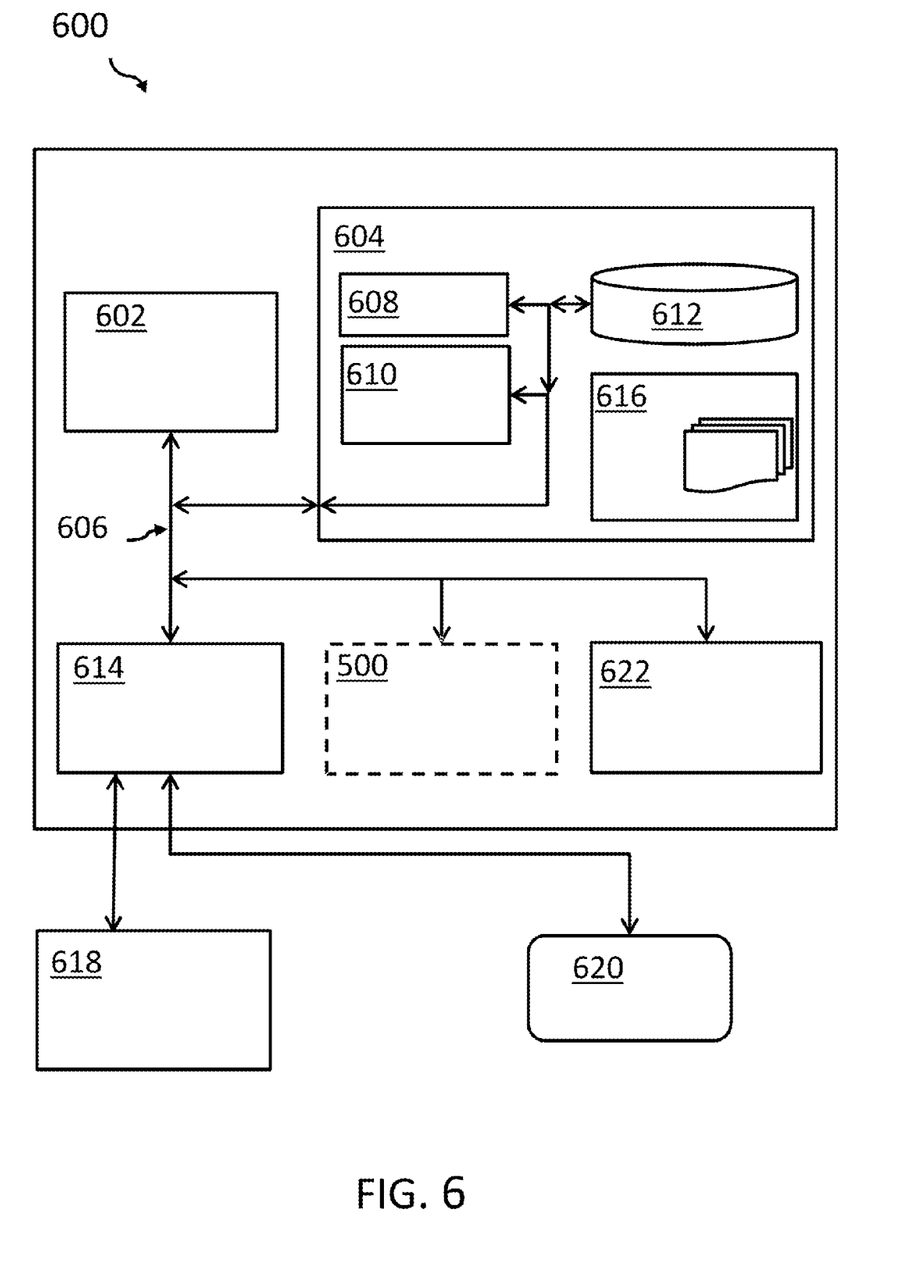
FIG. 6 illustrates one exemplary embodiment of a computer system that comprises the prediction system according to FIG. 5.

FIG. 6 illustrates a diagram of a computer system 600 that may comprise at least parts of the prediction system. Embodiments of the concept proposed here may in principle be used with practically any type of computer, regardless of the platform used therein to store and/or execute program codes. FIG. 6 illustrates by way of example a computer system 600 that is suitable for executing program code according to the method presented here. A computer system already present in a surgical microscope may also serve as a computer system for implementing the concept presented here, possibly with corresponding expansions.

The computer system 600 has a plurality of general-purpose functions. The computer system may in this case be a tablet computer, a laptop/notebook computer, some other portable or mobile electronic device, a microprocessor system, a microprocessor-based system, a smartphone, a computer system with specially configured special functions, or else a constituent part of a microscope system. The computer system 600 may be configured so as to execute computer system-executable instructions—such as for example program modules—that may be executed in order to implement functions of the concepts proposed here. For this purpose, the program modules may comprise routines, programs, objects, components, logic, data structures etc. in order to implement particular tasks or particular abstract data types.

The components of the computer system may comprise the following: one or more processors or processing units 602, a storage system 604 and a bus system 606 that connects various system components, including the storage system 604, to the processor 602. The computer system 600 typically has a plurality of volatile or non-volatile storage media accessible by the computer system 600. The storage system 604 may store the data and/or instructions (commands) of the storage media in volatile form—such as for example in a RAM (random access memory) 608—in order to be executed by the processor 602. These data and instructions realize one or more functions and/or steps of the concept presented here. Further components of the storage system 604 may be a permanent memory (ROM) 610 and a long-term memory 612, in which the program modules and data (reference sign 616) and also workflows may be stored.

The computer system comprises a number of dedicated devices (keyboard 618, mouse/pointing device (not illustrated), visual display unit 620, etc.) for communication purposes. These dedicated devices may also be combined in a touch-sensitive display. An I/O controller 614, provided separately, ensures a frictionless exchange of data with external devices. A network adapter 622 is available for communication via a local or global network (LAN, WAN, for example via the Internet). The network adapter may be accessed by other components of the computer system 600 via the bus system 606. It is understood in this case, although it is not illustrated, that other devices may also be connected to the computer system 600.

In addition, at least parts of the prediction system 500 for predicting digital images in the form of a digital fluorescence representation together with a further derived representation by means of a combined machine learning system can be connected to the bus system 606. The prediction system 500 and the computer system 600 may optionally use the memories and/or the processor(s) jointly.

The description of the various exemplary embodiments of the present invention has been given for the purpose of improved understanding, but does not serve to directly restrict the inventive concept to these exemplary embodiments. A person skilled in the art will himself/herself develop further modifications and variations. The terminology used here has been selected so as to best describe the basic principles of the exemplary embodiments and to make them easily accessible to a person skilled in the art.

The principle presented here may be embodied as a system, as a method, combinations thereof and/or else as a computer program product. The computer program product may in this case comprise one (or more) computer-readable storage medium/media having computer-readable program instructions in order to cause a processor or a control system to implement various aspects of the present invention.

As media, electronic, magnetic, optical, electromagnetic or infrared media or semiconductor systems are used as forwarding medium; for example SSDs (solid state devices/drives as solid state memory), RAM (random access memory) and/or ROM (read-only memory), EEPROM (electrically erasable ROM) or any combination thereof. Suitable forwarding media also include propagating electromagnetic waves, electromagnetic waves in waveguides or other transmission media (for example light pulses in optical cables) or electrical signals transmitted in wires.

The computer-readable storage medium may be an embodying device that retains or stores instructions for use by an instruction executing device. The computer-readable program instructions that are described here may also be downloaded onto a corresponding computer system, for example as a (smartphone) app from a service provider via a cable-based connection or a mobile radio network.

The computer-readable program instructions for executing operations of the invention described here may be machine-dependent or machine-independent instructions, microcode, firmware, status-defining data or any source code or object code that is written for example in C++, Java or the like or in conventional procedural programming languages such as for example the programming language "C" or similar programming languages. The computer-readable program instructions may be executed in full by a computer system. In some exemplary embodiments, there may also be electronic circuits, such as, for example, programmable logic circuits, field-programmable gate arrays (FPGAs) or programmable logic arrays (PLAs), which execute the computer-readable program instructions by using status information of the computer-readable program instructions in order to configure or to individualize the electronic circuits according to aspects of the present invention.

The invention presented here is furthermore illustrated with reference to flowcharts and/or block diagrams of methods, devices (systems) and computer program products according to exemplary embodiments of the invention. It should be pointed out that practically any block of the flowcharts and/or block diagrams can be embodied as computer-readable program instructions.

The computer-readable program instructions can be made available to a general purpose computer, a special computer or a data processing system programmable in some other way, in order to produce a machine, such that the instructions that are executed by the processor or the computer or other programmable data processing devices generate means for implementing the functions or processes illustrated in the flowchart and/or block diagrams. These computer-readable program instructions can correspondingly also be stored on a computer-readable storage medium.

In this sense any block in the illustrated flowchart or block diagrams can represent a module, a segment or portions of instructions representing a plurality of executable instructions for implementing the specific logic function. In some exemplary embodiments, the functions represented in the individual blocks can be implemented in a different order-optionally also in parallel.

The illustrated structures, materials, sequences and equivalents of all means and/or steps with associated functions in the claims hereinafter are intended to apply all structures, materials or sequences as expressed by the claims.

REFERENCE SIGNS 100 method (prediction phase)
102 method step of 100
104 method step of 100
200 extended exemplary embodiment
202 training phase
204 providing
206 providing
208 training
300 exemplary embodiment
302 training phase
304 prediction phase
306 learning system
308 first training images
310 second training images
312 indications about diseased tissue/training images
314 learning model
316 trained combined learning system
318 first digital image (white light recording)
320 fluorescence image
322 further representation
322-1 severities
322-2 tumour type
324 overlapping representation
400 exemplary embodiment
402 tissue (sample)
404 digital image recording unit
406 white light recording
408 learning system (e.g. U-net)
410 fluorescence image
412 learning system (e.g. U-net)
414 segmentation data/optical indications
416 learning system
418 learning system
500 prediction system
502 memory
502 processor
504 memory
506 system
508 prediction module
510 1st providing module
512 2nd providing module
514 training module
516 bus system
600 computer system
602 processor(s)
604 storage system
606 bus system
608 RAM
610 ROM
612 long-term memory
614 I/O controller
616 program modules and data
618 keyboard
620 visual display unit
622 network adapter

The invention claimed is:

1. A computer-implemented method comprising:
obtaining a first digital image of a tissue sample that was recorded under white light using a microsurgical optical system and a digital image recording unit; and
processing, using a combined machine learning system comprising a combined machine learning model, the first digital image to predict a second digital image of the tissue sample in a fluorescence representation, and a further representation comprising optical indications identifying diseased tissue elements, wherein the combined machine learning model is trained by:
obtaining a plurality of first digital training images of tissue samples that were recorded under white light using a microsurgical optical system;
obtaining a plurality of second digital training images in a fluorescence representation, which represent the same tissue samples as the plurality of first digital training images and comprise metainformation about diseased tissue elements; and
training the combined machine learning model for predicting the second digital image and the further representation based on the plurality of first digital training images as input and the plurality of second digital training images as ground truths.

2. The method of claim 1, wherein the digital image recording unit is configured to process three or four color channels.

3. The method of claim 1, wherein the combined machine learning model is trained to simultaneously predict both the second digital image in the fluorescence representation and the further representation, the further representation comprising at least one optical highlighting.

4. The method of claim 3, further comprising presenting the digital second image in the fluorescence representation and the at least one optical highlighting in one view.

5. The method of claim 1, wherein the combined machine learning model is trained to predict the further representation from the second digital image in the fluorescence representation.

6. The method of claim 1, wherein the further representation is a third digital image overlaid on the second digital image.

7. The method of claim 1, wherein the combined machine learning model comprises an encoder-decoder model or a classification network.

8. The method of claim 7, wherein the encoder-decoder model comprises a U-net convolutional neural network.

9. The method of claim 1, wherein the further representation comprises an indication concerning at least one of a tumour type or a tumour severity.

10. The method of claim 1, wherein the fluorescence representation of each of the plurality of second digital training images is obtained using a contrast agent in the tissue samples and illuminating the tissue samples with light of a predetermined wavelength.

11. The method of claim 1, wherein the metainformation about diseased tissue elements in the plurality of second digital training images comprises at least one optical highlighting of the diseased tissue elements.

12. The method of claim 1, wherein the metainformation about diseased tissue elements in the plurality of second digital training images comprises a predicted class of a tumour grade.

13. The method of claim 1, wherein the metainformation about diseased tissue elements in the plurality of second digital training images comprises a plurality of third digital training images.

14. A prediction system comprising:
a microsurgical optical system with a digital image recording unit configured to provide a first digital image of a tissue sample that was recorded under white light; and
a prediction module configured to process, using a combined machine learning system comprising a combined machine learning model, the first digital image to predict a second digital image of the tissue sample in a fluorescence representation, and a further representation comprising optical indications identifying diseased tissue elements wherein the further representation comprises an indication concerning at least one of a tumor type or a tumor severity, and wherein the combined machine learning model is trained by:
obtaining a plurality of first digital training images of tissue samples that were recorded under white light using a microsurgical optical system;
obtaining a plurality of second digital training images in a fluorescence representation, which represent the same tissue samples as the plurality of first digital training images and comprise metainformation about diseased tissue elements; and
training the combined machine learning model for predicting the second digital image and the further representation based on the plurality of first digital training images as input and the plurality of second digital training images as ground truths.

15. The prediction system of claim 14, wherein the second digital image in the fluorescence representation and the optical indications are represented within one view.

16. The prediction system of claim 14, wherein the combined machine learning model is trained to predict the further representation from the second digital image in the fluorescence representation.

17. The prediction system of claim 14, wherein the combined machine learning model comprises an encoder-decoder model or a classification network.

18. A non-transitory computer program product comprising a non-transitory computer-readable storage medium having program instructions stored thereon, the program instructions being executable by one or more processors or processing units to carry out the method of claim 1.

* * * * *